US012685801B2

(12) United States Patent
Kluge et al.

(10) Patent No.: US 12,685,801 B2
(45) Date of Patent: Jul. 21, 2026

(54) TWO-COMPONENT SYSTEM FOR THE IN SITU PREPARATION OF AN ARTIFICIAL CARTILAGE

(71) Applicant: HERAEUS MEDICAL GMBH, Wehrheim (DE)

(72) Inventors: Thomas Kluge, Wehrheim (DE); Christian Wahnes, Wehrheim (DE); Harro Antheunis, Beek-Ubbergen (NL)

(73) Assignee: Heraeus Medical GmbH, Wehrheim (DE)

( * ) Notice: Subject to any disclaimer, the term of this patent is extended or adjusted under 35 U.S.C. 154(b) by 956 days.

(21) Appl. No.: 17/616,434

(22) PCT Filed: May 27, 2020

(86) PCT No.: PCT/EP2020/064632
§ 371 (c)(1),
(2) Date: Dec. 3, 2021

(87) PCT Pub. No.: WO2021/004688
PCT Pub. Date: Jan. 14, 2021

(65) Prior Publication Data
US 2022/0233747 A1 Jul. 28, 2022

(30) Foreign Application Priority Data

Jul. 8, 2019 (EP) ..................................... 19184919

(51) Int. Cl.
| | |
|---|---|
| *A61L 27/26* | (2006.01) |
| *A61L 27/52* | (2006.01) |
| *A61L 27/54* | (2006.01) |
| *C08L 33/08* | (2006.01) |

(52) U.S. Cl.
CPC .............. *A61L 27/26* (2013.01); *A61L 27/52* (2013.01); *A61L 27/54* (2013.01); *C08L 33/08* (2013.01); *A61L 2300/232* (2013.01); *A61L 2300/406* (2013.01); *A61L 2300/802* (2013.01); *A61L 2400/06* (2013.01); *A61L 2430/06* (2013.01)

(58) Field of Classification Search
None
See application file for complete search history.

(56) References Cited

U.S. PATENT DOCUMENTS

| | | | | |
|---|---|---|---|---|
| 6,057,376 | A * | 5/2000 | Bass ........................... | C08J 9/28 521/142 |
| 2005/0112186 | A1 | 5/2005 | Devore et al. | |
| 2008/0248086 | A1* | 10/2008 | Asgari .................... | A61L 27/58 424/426 |
| 2018/0223329 | A1 | 8/2018 | Elisseeff et al. | |
| 2018/0243480 | A1* | 8/2018 | Martin .................... | A61L 27/54 |

FOREIGN PATENT DOCUMENTS

EP 2389925 A2 11/2011

OTHER PUBLICATIONS

Biological Buffers (2008), obtained from the Internet at http://www.applichem.com/fileadmin/-Broschueren/BioBuffer.pdf on Feb. 21, 2025. (Year: 2025).*
International Search Report and Written Opinion mailed Sep. 1, 2020 by the European Patent Office in its capacity as International Searching Authority for counterpart International Patent Application No. PCT/EP2020/064632.

* cited by examiner

*Primary Examiner* — David J Blanchard
*Assistant Examiner* — Daniel F Coughlin
(74) *Attorney, Agent, or Firm* — Dicke, Billig & Czaja, PLLC

(57) ABSTRACT

The invention relates to a two-component system for the in situ preparation of a polymer network by polymerizing acrylate monomers in the presence of a redox initiator couple comprising an activator and an initiator, the system comprising —a first container with a first component, which first component comprises the activator; and —a second container with a second component, which second component comprises the initiator; wherein the activator and/or the initiator is dissolved in an aqueous buffer solution; and wherein one or both containers further comprise —a water soluble acrylic monomer having one acrylate group; and —a water soluble acrylic monomer having two or more acrylate groups; and —at least one glycosaminoglycan; and wherein the combined water content in both containers is at least 50 wt. %, based on the total weight of the contents of both containers.

25 Claims, No Drawings

TWO-COMPONENT SYSTEM FOR THE IN SITU PREPARATION OF AN ARTIFICIAL CARTILAGE

The invention relates to a two-component system for the in situ preparation of a polymer network, to a method for preparing such polymer network, and to a polymer network.

Cartilage is a resilient and smooth elastic tissue that is found in many body parts. For example, it covers and protects the ends of bones which are linked by a joint such as the knee or the shoulder. In this way, the direct friction between the bones in a joint is prevented. Cartilage in joints may however become damaged due to aging, joint injury and/or exertion of repetitive and high loads on a joint. Such damage in a joint is known as an (osteo)chondral defect. This will cause inflammation in the joint, resulting in pain (arthralgia). This often leads to a reduced movability and flexibility of the body and therefore also to a lower quality of life of a person suffering from an (osteo)chondral defect. Unfortunately, cartilage has a poor regenerative capacity because it lacks blood vessels. A known strategy to cure (osteo)chondral defects is therefore to introduce artificial cartilage into a joint. As used herein, the term "(osteo) chondral defect" comprises a chondral defect and/or an osteochondral defect. A chondral defect refers to a damage to the articular cartilage, i.e. the cartilage that lines the end of the bones. An osteochondral defect refers to a damage that involves both the cartilage and a piece of underlying bone.

Materials that are often used as an artificial cartilage are polyacrylate-based hydrogels. Many of such materials have the disadvantage, however, that they cannot be prepared under physiological conditions; or, in the event that this is possible, the hydrogels do not have the desired properties.

Preparation under physiological conditions would require the injection of liquid precursors into the joint, so that their reaction occurs in situ. After the reaction has reached completion, the resulting hydrogel would be in place and would have adopted the desired shape. Systems that work in this manner and produce satisfactory hydrogels are however not yet available. On the other hand, systems wherein the hydrogel preparation occurs outside the body require tedious shaping steps. At the same time, the introduction of the resulting shape into the joint is much more invasive than when an injection is used.

In many current methods, the polymerization relies on curing with UV-light. This is undesired when the hydrogel is prepared in situ, because the UV-light is absorbed by intermediate tissue such as skin and bone. This makes it complicated to reach the appropriate intensity of UV-light at the right place, which leads to hydrogels with non-optimal properties.

Another challenge in the design of systems for in situ polymerization is how to arrive at the appropriate viscosity of the mixture of components at the time the polymerization starts. A too low viscosity will have the effect that the liquid seeps out of the cavity that is to be filled with the artificial cartilage. A too high viscosity would make it difficult or impossible to apply the liquid, for example by using a syringe.

Yet another challenge is to avoid the use of constituents that exhibit reactivity towards other constituents, towards body tissue and/or towards other biological material that is present at the site of injection. Many known systems (such as described in e.g. EP2389925 A2) rely on the use of nucleophiles that exhibit such reactivity. For example, the N-hydroxysuccinimide-moiety is often used, which reacts with e.g. amino groups. The in situ polymerization of such systems is therefore less controlled, which negatively affects the reproducibility of the polymerizations and yields inferior polymer products. Also, the choice of other constituents in the system is limited due to this reactivity of the N-hydroxysuccinimide-moiety; for example anti-bacterial agents with amino groups such as gentamycin have to be excluded from such systems.

A desired mechanical property that is not met by many known in situ prepared materials is a low degree of swelling. When an injected reaction mixture swells during the course of the reaction, it causes pressure build-up in the cavity of the joint and may ultimately block proper functioning of the joint. Many known systems for in situ generation exhibit a high degree of swelling, which makes these systems unsuitable for an in situ hydrogel generation.

Another property that is important for an artificial cartilage is that it has an open structure (i.e. a large free volume) and/or large pores. An open structure allows for the accommodation of blood clots including stem cells, while larger pores increase the accessibility of blood cells to inner parts of the polymer network. This is important for the healing of the joint because the presence of blood (stem) cells in inner parts of the artificial cartilage facilitates the formation of new tissue that ultimately replaces the artificial cartilage.

It is therefore an objective of the present invention to provide a polyacrylate-based artificial cartilage which can be prepared under physiological conditions without the use of a curing step with (UV-)light. It is also an object that the mixture of components has an appropriate viscosity at the beginning of the polymerization and/or that only limited swelling occurs during the polymerization. It is a further object that the final polyacrylate has a high porosity (a high free volume).

It has now been found that one or more of these objectives can be reached by using a particular two-component system. Accordingly, the present invention relates to a two-component system for the in situ preparation of a polymer network, in particular a hydrogel, by polymerizing acrylate monomers in the presence of a redox initiator couple comprising an activator and an initiator.

In particular, the present invention provides the following preferred embodiments.

1. A two-component system for the in situ preparation of a polymer network by polymerizing acrylate monomers in the presence of a redox initiator couple comprising an activator and an initiator, the system comprising a first container with a first component, which first component comprises the activator; and a second container with a second component, which second component comprises the initiator; wherein the activator and/or the initiator is dissolved in an aqueous buffer solution; and wherein one or both containers further comprise a water soluble acrylic monomer having one acrylate group; and a water soluble acrylic monomer having two or more acrylate groups; and at least one glycosaminoglycan; and wherein the combined water content in both containers is at least 50 wt. %, based on the total weight of the contents of both containers.

2. The two-component system according to item 1, wherein the first component and the second component are completely water-soluble.

3. The two-component system according to any of the previous items, wherein one or both containers further comprise an antibacterial agent, in particular an aminoglycoside such as gentamicin and/or a glycopeptide such as vancomycin.

4. The two-component system according to any of the previous items, wherein the at least one glycosaminoglycan is selected from the group of heparin, heparan sulfate, chondroitin sulfate, dermatan sulfate, keratan sulfate and hyaluronic acid.

5. The two-component system according to any of the previous items, wherein the two or more acrylate monomers comprise a monomer selected from the group of 2-hydroxyethyl methacrylate, acrylamide, 2-carboxyethyl acrylate, 2-(dimethylamino)propyl acrylate, methacrylamide, [2-(acryloyloxy)ethyl]trimethylammonium chloride, N-[Tris(hydroxymethyl) methyl]acrylamide, 3-sulfopropyl acrylate, in particular a salt thereof, 2-(diethylamino)ethyl methacrylate, diacetone acrylamide and N-[3-(dimethylamino)propyl]methacrylamide.

6. The two-component system according to any of the previous items, wherein the at least one monomer having two or more acrylate groups is a poly(1,3-glycerolate) diacrylate or a poly(ethylene glycol) diacrylate.

7. The two-component system according to any of the previous items, comprising a diacrylate having a number average molecular mass ($M_n$) of 10.000 g/mol or lower, in particular a number average molecular mass ($M_n$) in the range of 100-1500 g/mol, wherein said number average molecular mass ($M_n$) is determined by SEC according to DIN 55672-1.

8. The two-component system according to any of the previous items, wherein the activator is selected from the group of N,N-dimethyl-p-toluidine, N,N-bis(2-hydroxyethyl)-p-toluidine, 2-(diethylamino)ethyl methacrylate, 2-(dimethylamino)propyl acrylate, N-[3-(dimethylamino)propyl]methacrylamide and tetramethylethylenediamine.

9. The two-component system according to any of the previous items, wherein the initiator is selected from the group of ammonium persulfate, cumene hydroperoxide and dibenzoyl peroxide.

10. The two-component system according to any of the previous items, wherein the composition of the first container and the second container is chosen in such manner that the two or more acrylic monomers are completely dissolved; and that the polymerization product that forms upon mixing the first component and the second component exhibits phase separation of the polymerization product and the aqueous buffer solution.

11. The two-component system according to any of the previous items, wherein the pH of the buffer solution in each container is in the range of 7.2 to 7.6.

12. The two-component system according to any of the previous items, wherein the activator comprises a tertiary amino group.

13. The two-component system according to any of the previous items for use in the treatment of an (osteo) chondral defect or a bone-related disease or condition.

14. A method for preparing a polymer network, in particular a hydrogel, comprising providing a two-component system according to any of items 1 to 12; then mixing the components of the first and the second container so that a polymerization reaction occurs wherein a network of a polyacrylate is formed.

15. The method according to item 14, comprising injecting the mixed contents of the first and the second container into a human body.

16. The method according to any of items 14 or 15, wherein the mixing causes phase separation between the polymerization product and the aqueous buffer solution.

17. A Polymer network comprising a cross-linked polymer of two or more acrylic monomers comprising a water soluble acrylic monomer having one acrylate group and a water soluble acrylic monomer having two or more acrylate groups;

water that is contained in the cross-linked polymer; and at least one glycosaminoglycan that is contained in the cross-linked polymer;

wherein the polymer network has a free volume fraction of at least 0.50, wherein the free volume fraction (FVF) is calculated as $$FVF = (1 - m_d/m_g)$$

wherein and is the mass of the cross-linked polymer after evaporation of all the water that is contained in it, and $m_g$ is the mass of the cross-linked polymer when it is saturated with water.

18. The polymer network according to item 17, wherein the cross-linked polymer is not dissolved in the water so as to form a two-phase system therewith.

19. The polymer network according to item 17, wherein the cross-linked polymer is dissolved in the water so as to form a hydrogel therewith.

20. The polymer network according to any of the items 17 to 19, wherein the cross-linked polymer is permeable for human blood cells.

21. The polymer network according to any of the items 17 to 20 for use in the treatment of an (osteo)chondral defect or a bone-related disease or condition.

A two-component system of the invention comprises a first container comprising the first component and a second container comprising the second component, each component having a content that differs from the content of the other component. When mixed, both components react to form a polymer network, in particular a hydrogel. Usually the system comprises a mixing chamber, wherein the mixing of both components is performed prior to the actual injection of the mixture in e.g. a body cavity. To this end, the first and the second container are preferably in the form of a syringe with a piston, so that their contents can simultaneously be injected into the mixing chamber. The mixing occurs in a time span that is short with respect to the period wherein the reaction reaches completion.

The mixing of the two components concerns the mixing of a liquid with a solid or the mixing of two liquids. One or both components are therefore a liquid. Usually, when a component is a liquid, it is a solution. The first component is then a solution of at least the activator, and/or the second component is then a solution of at least the initiator. Other constituents in one or both solutions are the acrylic monomer and the at least one glycosaminoglycan. These and any other optional constituents may in principle be present in any of the two containers, provided that none of the constituents interferes with any other constituents in a negative way.

The water content in the mixture that is obtained by combining the first and the second component is at least 50 wt. %. Therefore, the combined water content in both containers also has to be at least 50 wt. %, based on the total weight of the contents of both containers. This is because such water content has the effect that the final polyacrylate has a structure that is sufficiently open and/or porous. The free volume of the obtained polymer network (in particular a hydrogel) has initially been occupied by the water during the formation of the polyacrylate. Therefore, the higher the water content during reaction (and thus the lower the concentration of the other constituents of the components), the higher the free volume of the polymeric product.

The aqueous solution(s) in a two-component system according to the invention are usually buffered solutions, i.e. the solution comprises one or more solute that provide the solution with a pH-buffering capacity. A buffer solution in one of the containers may, independently of an eventual other buffer solution in the other container, be selected from the group of carbonate buffer solution, acetate buffer solution, borate buffer solution, ammonium buffer solution, citric acid buffer solution, phosphate buffer solution, 2-(N-morpholino)ethanesulfonic acid buffer solution (MES), 2-[Bis(2-hydroxyethyl)amino]-2-(hydroxymethyl)propane-1,3-diol buffer solution (bis-tris methane; BTM), 2-[(2-amino-2-oxoethyl)amino]acetic acid buffer solution (ADA), N-(2-Acetamido)-2-aminoethanesulfonic acid buffer solution (ACES), 1,3-bis(tris(hydroxymethyl)methylamino)propane buffer solution (bis-tris propane; BTP), piperazine-N,N'-bis(2-ethanesulfonic acid) buffer solution (PIPES), 3-morpholino-2-hydroxypropanesulfonic acid buffer solution (MOPSO), cholamine chloride hydrochloride, 3-(N-morpholino)propanesulfonic acid buffer solution (MOPS), N,N-bis(2-hydroxyethyl)-2-aminoethanesulfonic acid buffer solution (BES), 2-[[1,3-dihydroxy-2-(hydroxymethyl)propan-2-yl]amino]ethanesulfonic acid buffer solution (TES), 4-(2-hydroxyethyl)-1-piperazineethanesulfonic acid buffer solution (HEPES), 3-(N,N-bis[2-hydroxyethyl]amino)-2-hydroxypropanesulfonic acid, N,N-bis(2-hydroxyethyl)-3-amino-2-hydroxypropanesulfonic acid buffer solution (DIPSO), 4-(N-morpholino)butanesulfonic acid buffer solution (MOBS), Acetamidoglycine buffer solution, 3[N-Tris(hydroxymethyl)methylamino]-2-hydroxypropanesulfonic acid buffer solution (TAPSO), triethanolamine buffer solutionTEA, piperazine-1,4-bis(2-hydroxypropanesulfonic acid) buffer solution (POPSO), 4-(2-Hydroxyethyl)piperazine-1-(2-hydroxypropanesulfonic acid) buffer solution (HEPPSO), 3-[4-(2-hydroxyethyl)piperazin-1-yl]propane-1-sulfonic acid buffer solution (HEPPS), N-(2-hydroxy-1,1-bis(hydroxymethyl)ethyl)glycine buffer solution (tricine), 2-amino-2-(hydroxymethyl)propane-1,3-diol buffer solution (Tris), 2-aminoacetam ide buffer solution (glycinamide), 2-[(2-aminoacetyl)amino]acetic acid buffer solution (glycylglycine), N-(2-hydroxyethyl)piperazine-N'-(4-butanesulfonic acid) buffer solution (HEPBS), 2-(bis(2-hydroxyethyl)amino)acetic acid buffer solution (bicine), 3-{[1,3-dihydroxy-2-(hydroxymethyl)propan-2-yl]amino}propane-1-sulfonic acid buffer solution (TAPS), 2-(cyclohexylamino)ethanesulfonic acid buffer solution (CHES), 2-amino-2-methyl-1-propanol buffer solution (AMP), N-(1,1-dimethyl-2-hydroxyethyl)-3-amino-2-hydroxypropanesulfonic acid buffer solution (AMPSO), 3-(cyclohexylamino)-2-hydroxy-1-propanesulfonic acid buffer solution (CAPSO), 3-(cyclohexylamino)-1-propanesulfonic acid buffer solution (CAPS), 4-(Cyclohexylamino)-1-butanesulfonic acid buffer solution (CABS).

The pH of the buffer solution in a container is chosen independently of the pH of the buffer solution in the other container. Usually, the pH of the buffer solution in each container is in the range of 7.2-7.6. In particular, the pH of the buffer solution in each container is chosen such that pH of the combined solutions is in the range of 7.2-7.6.

The activator may in principle be any compound that can activate a particular initiator (vide infra) when the activator is dissolved in an aqueous solution that comprises at least 50 wt. % of water. In a system of the invention, the activator preferably comprises a tertiary amino group. Such activator is for example selected from the group of N,N-dimethyl-p-toluidine, N,N-bis(2-hydroxyethyl)-p-toluidine, 2-(diethylamino)ethyl methacrylate, 2-(dimethylamino)propyl acrylate, N-[3-(dimethylamino)propyl]methacrylamide and tetramethylethylenediamine.

The activator may also fulfill a second role in that it may be one of the acrylate monomers that participates in the polymerization reaction when both components of the system of the invention are mixed. To this end, the activator comprises an acrylate group as in e.g. 2-(diethylamino)ethyl methacrylate, 2-(dimethylamino)propyl acrylate and N-[3-(dimethylamino)propyl] methacrylamide. A monomer that also has the function of activator should not be placed in the same container as the initiator.

A second role of the activator may also be the role of buffer. In particular, buffers having a tertiary amine group may also function as an activator. For example, when a buffer solution of (4-(2-hydroxyethyl)-1-piperazineethanesulfonic acid) is used (also known as HEPES), the polymerization reaction of the two-component system of the invention can be performed without the presence of a separate activator. A buffer that also has the function of activator should not be placed in the same container as the initiator.

The initiator may in principle be any compound that can initiate a polymerization reaction between the acrylic monomers (vide infra) contained in a system of the invention, when the initiator is dissolved in an aqueous solution that comprises at least 50 wt. % of water. Such activator is for example selected from the group of peroxides such as diethyl peroxide, di-tert-butyl peroxide, and dibenzyl peroxide; hydroperoxides such as methyl hydroperoxide, ethyl hydroperoxide, cumene hydroperoxide, benzyl hydroperoxide and tert-butylhydroperoxide; carboxylic acid peroxides such as dibenzoyl peroxide; acyloins such as benzoin; $\alpha,\alpha'$-azobisisobutyronitrile; $\gamma,\gamma'$-azobis($\gamma$-cyanovaleric acid); peroxyacids such as persulfates, peracetic acid, and peroxybenzoic acid; peroxalates such as dimethyl peroxalate and di(tert-butyl) peroxalate; disulfides and ketone peroxides. Preferably, the initiator is selected from the group of ammonium persulfate, cumene hydroperoxide and dibenzoyl peroxide.

A two-component system according to the invention comprises a monofunctional acrylic monomer (i.e. a compound having one acrylate group, a monoacrylate) as well as a polyfunctional acrylate monomer (i.e. a compound having at least two acrylate groups, e.g. three, four or five acrylate groups). By choosing an appropriate molar ratio between these two, the properties of the resulting polymer network (in particular a hydrogel) can be optimized.

The monoacrylate and the diacrylate are usually present in a molar ratio in the range of 1000:1 to 0.2:1. Preferably, the monoacrylate:diacrylate ratio is in the range of 500:1 to 5:1.

Preferably, the monoacrylate is selected from the group of 2-hydroxyethyl methacrylate, acrylamide, 2-carboxyethyl acrylate, 2-(dimethylamino)propyl acrylate, methacrylamide, [2-(acryloyloxy)ethyl]trimethylammonium chloride, N-[Tris(hydroxymethyl)methyl]acrylamide, 3-sulfopropyl acrylate, in particular a salt thereof, 2-(diethylamino)ethyl methacrylate, diacetone acrylamide and N-[3-(dimethyl-amino)propyl]methacrylamide.

Acrylates having two or more acrylate groups may in principle be any acrylate that is water soluble. Such acrylate may be an alkanediol diacrylate, i.e. one that has an alkane backbone between both acrylate groups. Additional hydroxyl or hydroxyalkyl groups may be present on the alkane backbone for improved water-solubility. On a hydroxyalkyl branch on the backbone an additional acrylate group may be present, so that the acrylate is e.g. a triacrylate or a tetraacrylate.

Usually, however, the acrylates having two or more acrylate groups are diacrylates. Preferably, such diacrylates are selected from the group of poly(1,3-glycerolate) diacrylates and poly(ethylene glycol) diacrylates.

The diacrylate preferably has a number average molecular mass ($M_n$) of 10.000 g/mol or lower, in particular a number average molecular mass ($M_n$) in the range of 100-1500 g/mol, more in particular in the range of 250-1000 g/mol.

The number average molecular mass (Mn) of the diacrylate can be determined by size exclusion chromatography according to standard DIN 55672-1 (March 2016) by comparison to commercially available PEG chromatography Mn standards at 25° C. The number average molecular weight is the statistical average molecular weight of all the molecules in the sample, and is defined by:

$$Mn = \Sigma N_i M_i / \Sigma N_i$$

where $M_i$ is the molecular weight of a molecule and $N_i$ is the number of chains of that molecular weight.

The acrylates are water soluble. For the purpose of the invention, by water soluble is meant that each of the acrylates has a water solubility of at least 1.0 wt. %. By a solubility of 1.0 wt. % is meant that in a 100 g aqueous solution of acrylate, 1.0 g of acrylate is dissolved. Preferably, the solubility of each acrylate is as high as possible. For example, it is at least 1.5 wt. %, at least 2.0 wt. %, at least 3.0 wt. %, at least 5.0 wt. %, at least 10.0 wt. %, at least 15.0 wt. %, at least 20 wt. % or at least 25 wt. %.

Typically, the sum of the solubilities of the acrylates is at least 2.0 wt. %. By a solubility of 2.0 wt. % is meant that in a 100 g aqueous solution of a plurality of acrylates, the total amount of dissolved acrylate is 2.0 g. Preferably, the sum of the solubilities of each acrylate is as high as possible. For example, the sum is at least 2.0 wt. %, at least 3.0 wt. %, at least 5.0 wt. %, at least 10.0 wt. %, at least 15.0 wt. %, at least 20 wt. % or at least 25 wt. %.

The acrylate monomers in the container (or containers) are usually completely dissolved (i.e. no undissolved monomer is present in the solution).

In one embodiment, both the first component and the second component are completely water-soluble. This means that the first component and the second component are, or can be, dissolved in, or in case of liquid substances mixed, with water, or an aqueous buffer solution such as phosphate-buffered saline (PBS, an aqueous solution comprising about 137 mM NaCl and about 3 mM KCl, buffered with phosphate to a pH of about 7.4), without any remaining solid, i.e. the solid components are substantially dissolvable in, or miscible with, water to the molecular or atomic level in a single aqueous phase. For example, the first component can be an aqueous solution, and the second component can be a powder that can be completely dissolved in water or an aqueous solution, such as the first component. In one embodiment, the first component can be an aqueous solution, and the second component can be a liquid that can be completely mixed with water or an aqueous solution, such as the first component.

In one embodiment, the second component can be an aqueous solution, and the first component can be a powder that can be completely dissolved in water or an aqueous solution, such as the second component. In one embodiment, the second component can be an aqueous solution, and the first component can be a liquid that can be completely mixed with water or an aqueous solution, such as the second component. It is also possible that the first component and/or the second component can comprise both a powder that can be completely dissolved in or mixed with water or an aqueous solution.

The above considerations on solubility refer to an amount of aqueous solution substantially identical to the combined quantity of aqueous solution that is present in the first component and the second component. In one embodiment, the first component and the second component can be combined to form an aqueous solution without any remaining solid, without adding any additional solvent.

In some embodiments, the first component and/or the second component do not comprise any organic solvent. An organic solvent, as described herein, refers to a liquid organic compound that mainly serves the purpose to dissolve other constituents of the first component and/or the second component. The acrylic monomers, activator, initiator, glycosaminoglycan, or antibacterial agent are not included in the scope of the term "organic solvent" as used herein.

Usually, the polymerization product that forms form the dissolved acrylates is also dissolved (in such cases, the product is a hydrogel). This is however not necessarily the case. Upon polymerization of the acrylates, the polarity decreases to a small extent due to the conversion of the unsaturated carbon-carbon double bond into a saturated moiety. This decrease may have the result that the polymer just reaches saturation and becomes insoluble under the conditions present. Especially when the dissolved monomer concentration prior to the polymerization was close to the concentration of saturation, the resulting polymer network may become insoluble and precipitate from the buffer solution. This may also be named a phase separation. In addition, such polymer network exhibits significantly less swelling upon contact with water than a corresponding hydrogel would do. The water-induced swelling of the phase-separated polyacrylates of the invention is typically less than 20%. This is advantageous for in situ application (e.g. at the site of the joint in a body), because the blood clots comprising stem cells are captured and natural healing can start directly from inside the polymer network. For a phase-separated polyacrylate, the water-solubility of the polyacrylate is usually in the range of 5-25 wt. %.

It is thus possible to choose those starting conditions that finally result in the formation of a phase-separated polymer. The skilled person is able to come to such conditions by routine experimentation without exerting inventive effort. Thus, in an embodiment, the composition of the first component and the second component is chosen in such manner that the two or more acrylic monomers are completely dissolved; and at least part of the polymerization product that forms upon mixing the contents of the first container and the contents of the second container exhibits phase separation of the polymerization product and the aqueous buffer solution.

A system of the invention comprises at least one glycosaminoglycan, which is an unbranched polysaccharide comprising a repeating disaccharide unit. It can be highly negatively charged and so impart high viscosity to the solution in which it resides. Glycosaminoglycans are located primarily on the surface of cells or in the extracellular matrix (ECM) but are also found in secretory vesicles in some types of cells. Along with their high viscosity comes low compressibility, which makes these molecules ideal for a lubricating fluid in the joints. At the same time, their rigidity provides structural integrity to cells and provides passageways between cells, allowing for cell migration. In a system of the invention, the at least one glycosaminoglycan is selected from the group of heparin, heparan sulfate, chondroitin sulfate, dermatan sulfate, keratan sulfate and hyaluronic acid.

A system of the invention preferably comprises at least one antibacterial agent, for example an aminoglycoside or a glycopeptide. The aminoglycoside may be selected from the group of kanamycin A, amikacin, tobramycin, dibekacin, gentamicin, sisomicin, netilmicin, neomycin B, neomycin C, neomycin E, streptomycin and gentamycin. The glycopeptide may be selected from the group of vancomycin, teicoplanin, telavancin, ramoplanin, decaplanin and bleomycin.

With the two-component system as described above, a polymer network (in particular a hydrogel) can easily be prepared by mixing the two components. Accordingly, the invention further relates to a method for preparing a polymer network, in particular a hydrogel, the method comprising providing a two-component system as described hereinabove, followed by mixing the contents of the first and the second container. After the mixing, the reaction starts. The method of the invention therefore typically requires that the mixture is allowed to react during a certain period of time, a process that may also be termed hardening. The components in the system are usually designed in such way that the reaction is complete within 60. Preferably, the reaction is complete within 45 minutes, more preferably within 30 minutes, and even more preferably within 20 minutes. For example, it may take 5-20 minutes for the reaction to be complete, or 5-15 minutes for the reaction to be complete or 5-10 minutes for the reaction to be complete.

The mixture is to be injected into a cavity of a (human) body well before it is hardened. This is because the more the progression of the polymerization reaction, the more difficult it is to transfer the mixture from the two-component system into the body cavity (by e.g. a needle); and because the mixture has to be capable of sufficiently spreading throughout the body cavity during its injection into that cavity. Therefore, it is preferably injected as soon as possible after the mixing is complete. When injected, the mixture preferably has a certain viscosity that allows a proper dispersion of the mixture in the body cavity (i.e. the viscosity is not too high) without seeping into neighboring locations where no artificial cartilage is desired (i.e. the viscosity is too low). Therefore, the initial dynamic viscosity of the mixture (i.e. the viscosity just after mixing both components) is preferably at least 0.5 Pa s.

The mixing of the contents is usually directly followed by injection into a body part of an organism, such as a human. Thus, the method may comprise injecting the mixed contents of the first and the second container into a body part of a human body. The body part is typically a joint such as a knee or elbow, but it may in principle be any body part that is in need of cartilage repair. In particular, an injection occurs into a body cavity of e.g. a joint.

Usually, the temperature of mixing is in the range of 10-40° C., in particular in the range of 20-40° C. When injected into an organism, the temperature of mixing is preferably close to the body temperature of the organism, for example within 2° C. from the body temperature, or within 1° C. When injected into a human, the temperature of mixing is preferably in the range of 36-38° C.

As elaborated above, the two-component system may be designed in such manner that phase separation between the polymerization product and the aqueous buffer solution occurs during the polymerization reaction. The invention further relates to a polymer network (in particular a hydrogel) obtainable by a method of the invention.

The invention further relates to a polymer network that is suitable for use as an artificial cartilage, the network comprising a cross-linked polymer of two or more acrylic monomers comprising a water soluble acrylic monomer having one acrylate group and a water soluble acrylic monomer having two or more acrylate groups;

water that is contained in the cross-linked polymer; and at least one glycosaminoglycan that is contained in the cross-linked polymer;

wherein the polymer network has a free volume fraction of at least 0.50, wherein the free volume fraction (FVF) is calculated as $$FVF = (1 - m_d/m_g)$$

wherein and is the mass of the cross-linked polymer after evaporation of all the water that is contained in it, and $m_g$ is the mass of the cross-linked polymer when it is saturated with water.

By the free volume is meant the volume that is created by the gaps that are present between polymer chains of the cross-linked polymer, to the extent that the gaps are available for (and capable of) being filled with water. When the cross-linked polymer is saturated with water, then this means that there is an equilibrium situation wherein the free volume is completely filled with water. For the purpose of the invention, the free volume fraction is defined as the fraction of the volume of the polymer network that is not occupied by chains of the cross-linked polymer. For convenience, this is approximated by using the mass fraction of the polymer network that is constituted by water. This fraction is obtained by determining the mass of the polymer network after evaporating all the water from the polymer network, followed by dividing by the mass of the cross-linked polymer when it is saturated with water. The result is then subtracted from 1 to yield the free volume fraction (FVF)

The free volume fraction (FVF) in a polymer network of the invention is at least 0.50. Usually, it is 0.60 or more. In particular, it is in the range of 0.70-0.99. More in particular, it is in the range of 0.90-0.98. Even more in particular, it is in the range of 0.95-0.975. A high free volume means that there is much space wherein blood cells can accumulate, so that the formation of new cartilage is stimulated over a larger volume of the cross-linked polymer.

The degree of swelling (DoS) is the quantified swelling that occurs when a freshly prepared (hardened) polymer network is left to equilibrate into an isotonic buffer. First, the free volume of a hardened gel ($FVF_h$) is determined just after hardening. After having been submerged in an isotonic buffer overnight, the free volume of the swollen gel ($FVF_s$) is determined. The degree of swelling is then calculated using the following equation:

$$DoS = FVF_s - FVF_h$$

The at least one glycosaminoglycan that is present in one or both components of the two-component system is also present in the cross-linked polymer. Preferably, it is entrapped in the cross-linked polymer, i.e. it cannot escape therefrom because its size is too large for the pores of the polymer to pass them.

In a polymer network of the invention, the cross-linked polymer is dissolved in the water, or it is not dissolved in the water (as is explained hereinabove). When dissolved, the water and the cross-linked polymer together form one phase (a hydrogel). When not dissolved, phase separation of the cross-linked polymer and the water has occurred, so that the cross-linked polymer forms a two-phase system with the water.

Thus, when dissolved, the polymer network of the invention is in fact a hydrogel. Accordingly, the present invention also relates to a hydrogel comprising a cross-linked polymer of two or more acrylic monomers comprising a water soluble acrylic monomer having one acrylate group and a water soluble acrylic monomer having two or more acrylate groups;

water that is contained in the cross-linked polymer so as to form a hydrogel therewith; and at least one glycosaminoglycan that is contained in the cross-linked polymer;

wherein the hydrogel has a free volume fraction of at least 0.50, wherein the free volume fraction (FVF) is calculated as $$FVF = (1 - m_d/m_g)$$

wherein and is the mass of the polymer network after evaporation of all the water that is contained in it, and $m_g$ is the mass of the polymer network when it is saturated with water.

When the resulting polymer is not dissolved in the aqueous buffer solution, then it has particular properties that are advantageous when applied as an artificial cartilage.

The polymer networks described herein preferably have physiological pH (such as about pH 7.4 to 7.5) and ion strength (such as about 140 to 150 mM NaCl).

EXAMPLES

1. Hydrogel

A dissolved polymer network of the invention (a hydrogel) was prepared by combining a first component and a second component. When combined, the mixture that results is the "hardening mixture". After hardening of this mixture, the final polymer network is formed.

Both components contained a buffer solution (10 mM phosphate buffered solution) comprising dissolved poly(ethylene glycol) diacrylate ($M_n$=700 g/mol; the cross-linking agent); and moderate pre-cross-linked hyaluronic acid (HA; the glycosaminoglycan).

The solution of the first component additionally contained dissolved 2-(dimethylamino)propyl acrylate (DMAPA; the monomer) as well as dissolved tetramethylethylenediamine (TEMED; the activator). The solution of the second component additionally contained ammonium persulfate (($NH_4$)$_2S_2O_8$, the initiator). The DMAPA monomer was not present in the solution of the second component, because it also functions as an activator and should therefore not be contacted with the initiator (and indeed, the polymerization reaction may also be carried out when the TEMED activator is absent).

The amounts of monomer, cross-linking agent, hyaluronic acid, and activator or initiator in each component were chosen such that the hardening mixture has the following composition:

69.00 wt. % of aqueous buffer solution;

15.00 wt. % of monomer;

14.85 wt. % of cross-linking agent;

1.00 wt. % of moderate pre-cross-linked hyaluronic acid;

0.10 wt. % of activator;

0.05 wt. % of initiator.

The 10 mM aqueous buffer solution contained 150 mM NaCl and 10 mM $Na_2HPO_4/NaH_2PO_4$.

Each component was prepared according to a procedure comprising the following steps:

weighing the solvent into a glass vial;

adding the cross-linking agent;

adding the monomer (only in the first component);

adding the activator (only in the first component);

adding the initiator (only in the second component);

homogenizing the resulting mixture for 30 seconds using a vortex mixer;

degassing the resulting solution for 10 minutes under vacuum in a vacuum oven (at 166 mbar or lower and at ambient temperature).

adding the pre-cross-linked hyaluronic acid to the solution;

stirring at 600 rpm using a micro-stirrer until a clear and colorless viscous solution is obtained (e.g. for 1 wt. % HA, stirring is continued for 1 hour).

degassing the final solution for 20 minutes under vacuum in a vacuum oven (at 166 mbar or lower and at ambient temperature).

To prepare the final polymer network of the invention, the two components were mixed, stirred for two minutes using a (micro) overhead stirrer. After that, the mixture was placed in a water bath at 37° C. for at least one hour.

The hardening appeared to be complete within one hour, yielding an orange transparent soft solid (a hydrogel) with a swelling of 9.1 wt. % and a free volume fraction of 0.90.

2. Phase-Separated Polymer Network Comprising Gentamicin

A phase-separated polymer network of the invention was prepared by combining a first component and a second component. When combined, the mixture that results is the "hardening mixture". After hardening of this mixture, the final polymer network is formed.

Both components contained a buffer solution (10 mM phosphate buffered solution) comprising dissolved 2-hydroxyethyl methacrylate (HEMA; the monomer);

dissolved poly(ethylene glycol) diacrylate ($M_n$=700 g/mol; the cross-linking agent); and dissolved gentamicin (saturated solution);

gentamicin-loaded pre-cross-linked hyaluronic acid (HA; the glycosaminoglycan).

The solution of the first component additionally contained dissolved tetramethylethylenediamine (TEMED; the activator); and the solution of the second component additionally contained ammonium persulfate (($NH_4$)$_2S_2O_8$, the initiator).

The amounts of monomer, cross-linking agent, hyaluronic acid, and activator or initiator in each component were chosen such that the hardening mixture has the following composition:

65.00 wt. % of aqueous buffer solution;

15.00 wt. % of monomer;

9.85 wt. % of cross-linking agent;

10.00 wt. % of gentamicin-loaded pre-cross-linked hyaluronic acid;

0.10 wt. % of activator;

0.05 wt. % of initiator.

The 10 mM aqueous buffer solution contained 150 mM NaCl and 10 mM $Na_2HPO_4/NaH_2PO_4$.

The pre-cross-linked hyaluronic acid was loaded with gentamicin by mixing an amount (mass) of pre-cross-linked HA with an equal amount (mass) of saturated gentamicin phosphate buffered solution.

Each component was prepared according to a procedure comprising the following steps:

weighing the solvent into a glass vial;

adding the cross-linking agent;

adding the monomer;

adding the activator (only in the first component);

adding the initiator (only in the second component);

homogenizing the resulting mixture for 30 seconds using a vortex mixer;

degassing the resulting solution for 10 minutes under vacuum in a vacuum oven (at 166 mbar or lower and at ambient temperature).

adding the gentamicin-loaded pre-cross-linked hyaluronic acid to the solution;

adding hyaluronic acid to the mixture;

stirring at 600 rpm using a micro-stirrer until a clear and colorless viscous solution is obtained (e.g. for 1 wt. % HA, stirring is continued for 1 hour).

degassing the final solution for 20 minutes under vacuum in a vacuum oven (at 166 mbar or lower and at ambient temperature).

To prepare the final polymer network of the invention, the two components were mixed, stirred for two minutes using a (micro) overhead stirrer. After that, the mixture was placed in a water bath at 37° C. for at least one hour.

The hardening appeared to be complete within one hour, yielding an opaque gel with a swelling of 1.4 wt. % and a free volume fraction of 0.71. Advantageously, the gel appeared to exhibit an unexpected release of gentamicin of more than 15 wt. % of the total loading of gentamicin in the first two days, increasing to 40 wt. % in the eight days thereafter.

The invention claimed is:

1. A two-component system for the in situ preparation of a polymer network by polymerizing acrylic monomers in the presence of a redox initiator couple comprising an activator and an initiator, the system comprising a first container that contains a first aqueous buffer solution comprising the activator; and a second container that contains a second aqueous buffer solution comprising the initiator;

wherein one or both of the first aqueous buffer solution and the second aqueous buffer solution further comprise a water soluble acrylic monomer having one acrylate group; and a water soluble acrylic monomer having two or more acrylate groups; and at least one glycosaminoglycan;

wherein the combined water content in both containers is at least 50 wt. %, based on the total weight of the contents of both containers, and wherein the acrylic monomer in the first container is completely dissolved in the first aqueous buffer solution and the acrylic monomer in the second container is completely dissolved in the second aqueous buffer solution.

2. The two-component system according to claim 1, wherein the contents of the first container and the contents of the second container are completely water-soluble.

3. The two-component system according to claim 1, wherein one or both containers further comprise an antibacterial agent selected from an aminoglycoside and glycopeptide.

4. The two-component system according to claim 1, wherein the at least one glycosaminoglycan is selected from the group of heparin, heparan sulfate, chondroitin sulfate, dermatan sulfate, keratan sulfate and hyaluronic acid.

5. The two-component system according to claim 1, comprising acrylic monomer selected from the group of 2-hydroxyethyl methacrylate, acrylamide, 2-carboxyethyl acrylate, 2-(dimethylamino) propyl acrylate, methacrylamide, [2-(acryloyloxy)ethyl]trimethylammonium chloride, N-[Tris(hydroxymethyl)methyl]acrylamide, 3-sulfopropyl acrylate, a salt thereof, 2-(diethylamino)ethyl methacrylate, diacetone acrylamide and N-[3-(dimethylamino)propyl] methacrylamide.

6. The two-component system according to claim 1, wherein at least one acrylic monomer having two or more acrylate groups is a poly(1,3-glycerolate) diacrylate or a poly(ethylene glycol) diacrylate.

7. The two-component system according to claim 1, comprising a diacrylate having a number average molecular mass $(M_n)$ of 10,000 g/mol or lower, in particular a number average molecular mass $(M_n)$ in the range of 100-1500 g/mol, wherein said number average molecular mass $(M_n)$ is determined by SEC according to DIN 55672-1.

8. The two-component system according to claim 1, wherein the activator is selected from the group of N,N-dimethyl-p-toluidine, N,N-bis(2-hydroxyethyl)-p-toluidine, 2-(diethylamino)ethyl methacrylate, 2-(dimethylamino)propyl acrylate, N-[3-(dimethylamino)propyl]methacrylamide and tetramethylethylenediamine.

9. The two-component system according to claim 1, wherein the initiator is selected from the group of ammonium persulfate, cumene hydroperoxide and dibenzoyl peroxide.

10. The two-component system according to claim 1, wherein the composition of the first container and the second container is chosen in such manner that the entire amount of acrylic monomers is completely dissolved in aqueous buffer solution in the first container or in the second container; and the polymerization product that forms upon mixing the first aqueous buffer solution and the second aqueous buffer solution exhibits phase separation of the polymerization product and the first and second aqueous buffer solution.

11. The two-component system according to claim 1, wherein the pH of the buffer solution in each container is in the range of 7.2 to 7.6.

12. The two-component system according to claim 1, wherein the activator comprises a tertiary amino group.

13. The two-component system according to claim 1 for treatment of a chondral defect or a bone-related disease or condition.

14. A polymer network comprising a cross-linked polymer of two or more acrylic monomers comprising a water soluble acrylic monomer having one acrylate group and a water soluble acrylic monomer having two or more acrylate groups;

water that is contained in the cross-linked polymer; and at least one glycosaminoglycan that is contained in the cross-linked polymer;

wherein the polymer network has a free volume fraction of at least 0.50, wherein the free volume fraction (FVF) is calculated as $$FVF = (1 - m_d/m_g)$$

wherein $m_d$ is the mass of the cross-linked polymer after evaporation of all the water that is contained in it, and $m_g$ is the mass of the cross-linked polymer when it is saturated with water, wherein the cross-linked polymer is dissolved in the water to form a hydrogel.

15. The polymer network according to claim 14, wherein the cross-linked polymer is permeable for human blood cells.

16. The polymer network according to claim 14 for treatment of a chondral defect or a bone-related disease or condition.

17. The two-component system of claim 1, wherein the first aqueous buffer solution and the second aqueous buffer solution are adapted to react to produce a polymer network having a free volume fraction of at least 0.60.

18. The two-component system according to claim 1, wherein the composition of the first container and the second container is chosen in such manner that the entire amount of acrylic monomers is completely dissolved in aqueous buffer solution in the first container or in the second container; and the polymerization product that forms upon mixing the first aqueous buffer solution and the second aqueous buffer solution is a hydrogel.

19. The two-component system of claim 1, wherein:

the contents of the first container consist of the first aqueous buffer solution, which is completely water-soluble; and the contents of the second container consist of the second aqueous buffer solution, which is completely water-soluble.

20. The two-component system of claim 1, wherein the monomer contained in the first container consists of water soluble acrylic monomers, and the monomer contained in the second container consists of water soluble acrylic monomer.

21. The polymer network of claim 14, wherein the cross-linked polymer is derived from acrylic monomers consisting of water soluble acrylic monomers having one acrylate group and water soluble acrylic monomers having two or more acrylate groups.

22. A two-component system for the in situ preparation of a polymer network by polymerizing acrylic monomers in the presence of a redox initiator couple comprising an activator and an initiator, the system comprising a first container that contains a first aqueous buffer solution comprising the activator; and a second container that contains a second aqueous buffer solution comprising the initiator;

wherein one or both of the first aqueous buffer solution and the second aqueous buffer solution further comprise a water soluble acrylic monomer having one acrylate group; and a water soluble acrylic monomer having two or more acrylate groups; and at least one glycosaminoglycan;

wherein the combined water content in both containers is at least 50 wt. %, based on the total weight of the contents of both containers, and wherein the total amount of water soluble acrylic monomer is at least 5.0 weight percent of the first and second aqueous buffer solutions.

23. The two-component system of claim 22, wherein the total amount of water soluble acrylic monomer is at least 15.0 weight percent of the first and second aqueous buffer solutions.

24. The two component system of claim 22, wherein the water soluble acrylic monomer having one acrylate group has a solubility of at least 20 weight percent; and the water soluble acrylic monomer having two or more acrylate groups has a solubility of at least 20 weight percent.

25. The two-component system of claim 22, adapted for the in situ preparation of a polymer network that is a hydrogel.

* * * * *